United States Patent
Sawada et al.

(10) Patent No.: US 9,149,292 B2
(45) Date of Patent: Oct. 6, 2015

(54) PROBE ADAPTED TO TREAT LIVING TISSUE AND ACTUATION METHOD OF DEVICE

(75) Inventors: Yukihiko Sawada, Yoshikawa (JP); Norihiro Yamada, Hino (JP)

(73) Assignee: OLYMPUS CORPORATION (JP)

( * ) Notice: Subject to any disclaimer, the term of this patent is extended or adjusted under 35 U.S.C. 154(b) by 0 days.

(21) Appl. No.: 13/531,745

(22) Filed: Jun. 25, 2012

(65) Prior Publication Data

US 2012/0330195 A1 Dec. 27, 2012

Related U.S. Application Data

(63) Continuation of application No. PCT/JP2011/075733, filed on Nov. 8, 2011.

(60) Provisional application No. 61/424,185, filed on Dec. 17, 2010.

(51) Int. Cl.
*A61H 1/00* (2006.01)
*A61B 17/32* (2006.01)

(52) U.S. Cl.
CPC .............................. *A61B 17/320092* (2013.01)

(58) Field of Classification Search
USPC ............................................................. 601/2
See application file for complete search history.

(56) References Cited

U.S. PATENT DOCUMENTS

| | | | |
|---|---|---|---|
| 5,695,510 A | 12/1997 | Hood | |
| 6,129,735 A | 10/2000 | Okada et al. | 606/169 |
| 7,229,455 B2 | 6/2007 | Sakurai et al. | 606/169 |
| 2003/0045887 A1 | 3/2003 | Sakurai et al. | 606/128 |
| 2003/0055340 A1* | 3/2003 | van Klooster | 600/459 |
| 2006/0094988 A1* | 5/2006 | Tosaya et al. | 601/2 |
| 2007/0244423 A1* | 10/2007 | Zumeris et al. | 604/22 |
| 2008/0232197 A1* | 9/2008 | Kojima et al. | 367/99 |
| 2009/0030311 A1 | 1/2009 | Stulen et al. | |

FOREIGN PATENT DOCUMENTS

| | | |
|---|---|---|
| JP | 63-309249 | 12/1988 |
| JP | 64-046447 | 2/1989 |

OTHER PUBLICATIONS

International Search Report mailed Dec. 27, 2011 in corresponding PCT International Application No. PCT/JP2011/075733.

(Continued)

*Primary Examiner* — Tse Chen
*Assistant Examiner* — Hien Nguyen
(74) *Attorney, Agent, or Firm* — Ostrolenk Faber LLP

(57) ABSTRACT

A probe which is configured for a treatment device which is configured to treat a body tissue using ultrasonic vibration, includes a base member which includes a base surface defined by a longitudinal direction and a width direction shorter than the longitudinal direction and which is a vibration-retardation member configured to hardly transmit the ultrasonic vibration, a waveguide main body which has a width smaller than a width of the base surface in a width direction, protrudes with respect to the base surface, and is extended along the longitudinal direction of the base surface, and an end effecter which is provided at a tip end portion of the waveguide main body and which is configured to treat the body tissue by the ultrasonic vibration transmitted through the waveguide main body.

14 Claims, 14 Drawing Sheets

(56) References Cited

OTHER PUBLICATIONS

Written Opinion mailed Dec. 27, 2011 in corresponding PCT International Application No. PCT/JP2011/075733.
Search Report issued by European Patent Office and received by applicant on Feb. 21, 2013 in connection with corresponding EP patent application No. EP 11 84 9037.
English translation of Search Report issued by European Patent Office and received by applicant on Feb. 21, 2013 in connection with corresponding EP patent application No. EP 11 84 9037.

* cited by examiner

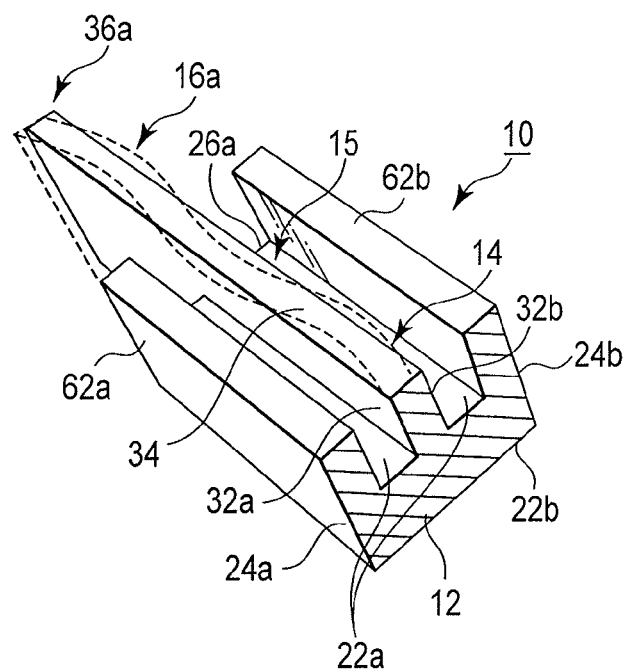
F I G. 4B
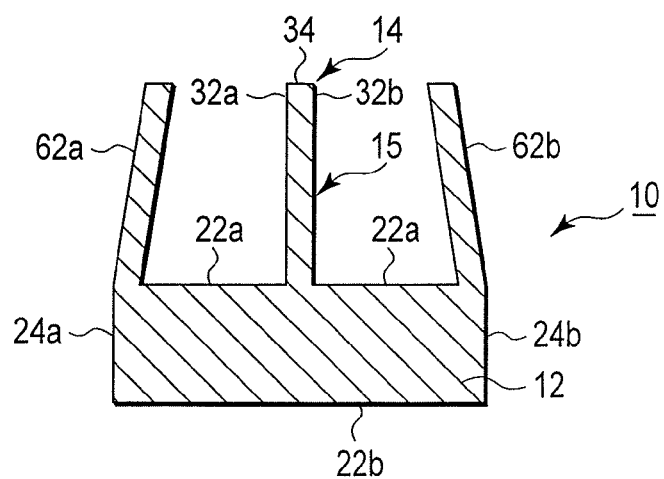
F I G. 4C

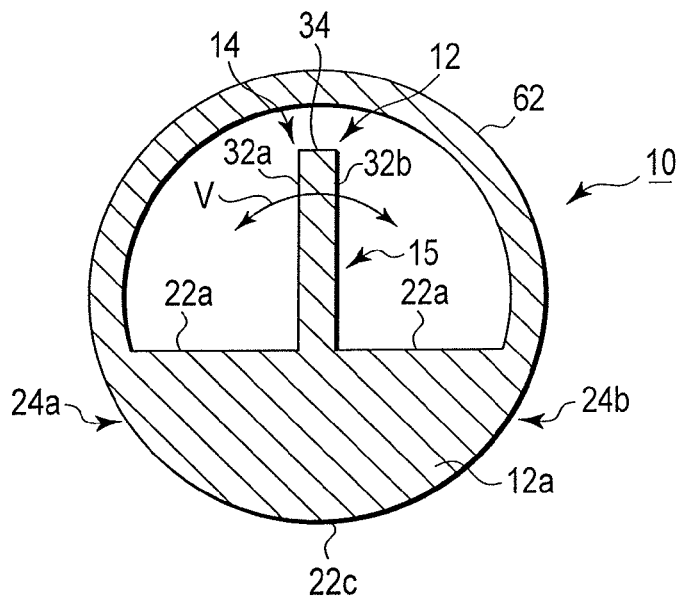
F I G. 5B
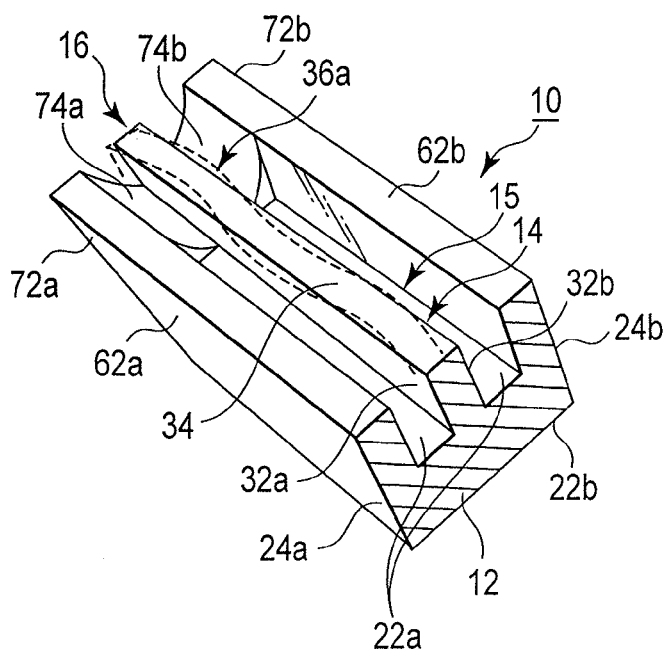
F I G. 6A

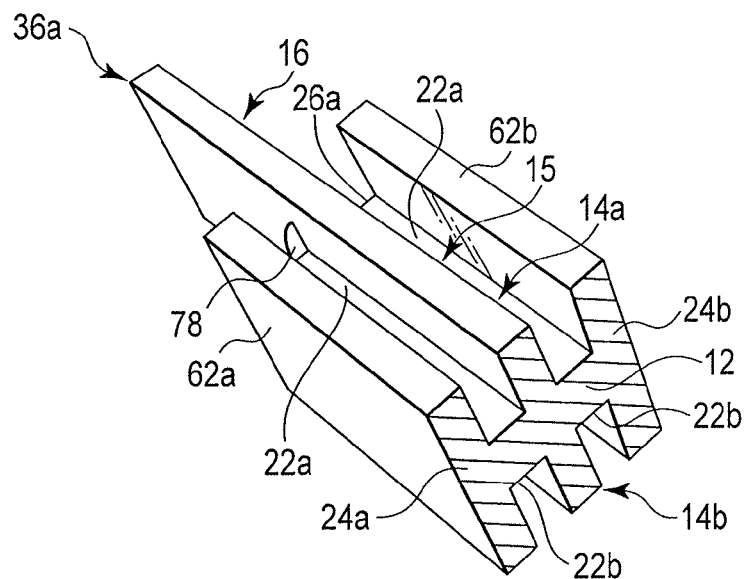
F I G. 9A
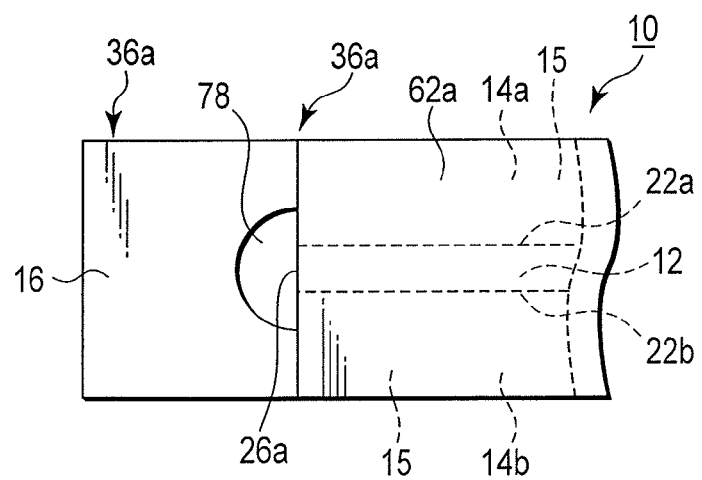
F I G. 9B

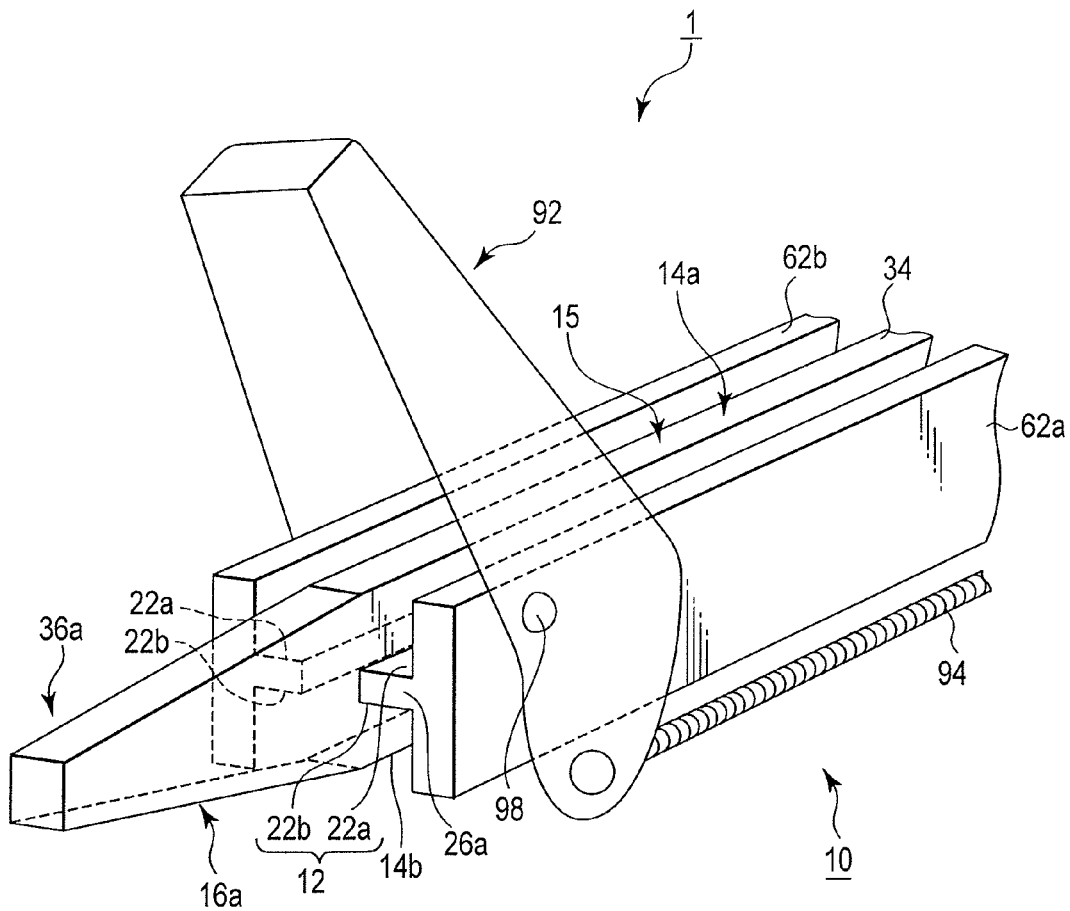
F I G. 11A
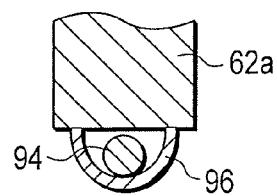
F I G. 11B

PROBE ADAPTED TO TREAT LIVING TISSUE AND ACTUATION METHOD OF DEVICE

CROSS-REFERENCE TO RELATED APPLICATIONS

This is a Continuation Application of PCT Application No. PCT/JP2011/075733, filed Nov. 8, 2011, which was published under PCT Article 21(2) in Japanese.

This application is based upon and claims the benefit of priority from prior Provisional Application No. 61/424,185, filed Dec. 17, 2010, the entire contents of which are incorporated herein by reference.

BACKGROUND OF THE INVENTION

1. Field of the Invention

The present invention relates to a probe which is configured to treat a body tissue by using ultrasonic vibration and relates to an actuation method of a device.

2. Description of the Related Art

For example, as disclosed in U.S. Pat. No. 6,129,735-A, an ultrasonic treatment device configured to treat a body tissue by using ultrasonic vibration generally has a longitudinal vibration type ultrasonic transducer appressed against a proximal end of an elongated rod-like probe. The ultrasonic transducer is vibrated, the vibration is thereby transmitted to the probe, a distal end of the probe is brought into contact with a body tissue, and various kinds of treatments are given. At this time, the probe and the ultrasonic transducer are coaxially provided, and the longitudinal vibration transmitted to the probe by the vibration of the ultrasonic transducer is mainly used to treat the body tissue.

For example, in U.S. Pat. No. 7,229,455-B2 is disclosed an ultrasonic treatment device having a torsional vibration type ultrasonic transducer that is able to generate torsional vibration.

BRIEF SUMMARY OF THE INVENTION

A probe which is configured for a treatment device which is configured to treat a body tissue using ultrasonic vibration, includes a base member which includes a base surface defined by a longitudinal direction and a width direction shorter than the longitudinal direction and which is a vibration-retardation member configured to hardly transmit the ultrasonic vibration; a waveguide main body which has a width smaller than a width of the base surface in a width direction, protrudes with respect to the base surface, and is extended along the longitudinal direction of the base surface; and an end effecter which is provided at a tip end portion of the waveguide main body and which is configured to treat the body tissue by the ultrasonic vibration transmitted through the waveguide main body.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4B is a schematic view showing the ultrasonic treatment device according to the second embodiment from an obliquely upper side and also showing a transverse cross section of the treatment device on a distal end side;

FIG. 4C is a schematic transverse cross-sectional view showing an ultrasonic treatment device according to a modification of the second embodiment;

FIG. 5B is a schematic transverse cross-sectional view showing an ultrasonic treatment device according to further modification of the second embodiment;

FIG. 6A is a schematic view showing an ultrasonic treatment device according to a third embodiment from an obliquely upper side and also showing a transverse cross section of the treatment device on a distal end side;

FIG. 9A is a schematic view showing an ultrasonic treatment device according to a modification of the fourth embodiment from an obliquely upper side and also showing a transverse cross section of the treatment device on a distal end side;

FIG. 9B is a side view of the distal end side of the ultrasonic treatment device according to the modification of the fourth embodiment;

FIG. 11A is a schematic perspective view showing a distal end side of an ultrasonic treatment device according to a fifth embodiment;

FIG. 11B is a schematic transverse cross-sectional view showing a state that a wire is arranged along a lower surface of a protective member of the ultrasonic treatment device according to the fifth embodiment.

DETAILED DESCRIPTION OF THE INVENTION

Embodiments of practicing the invention will be described with reference to the drawings.

A first embodiment will now be described with reference to FIG. 1A to FIG. 3.

Figure 1A:
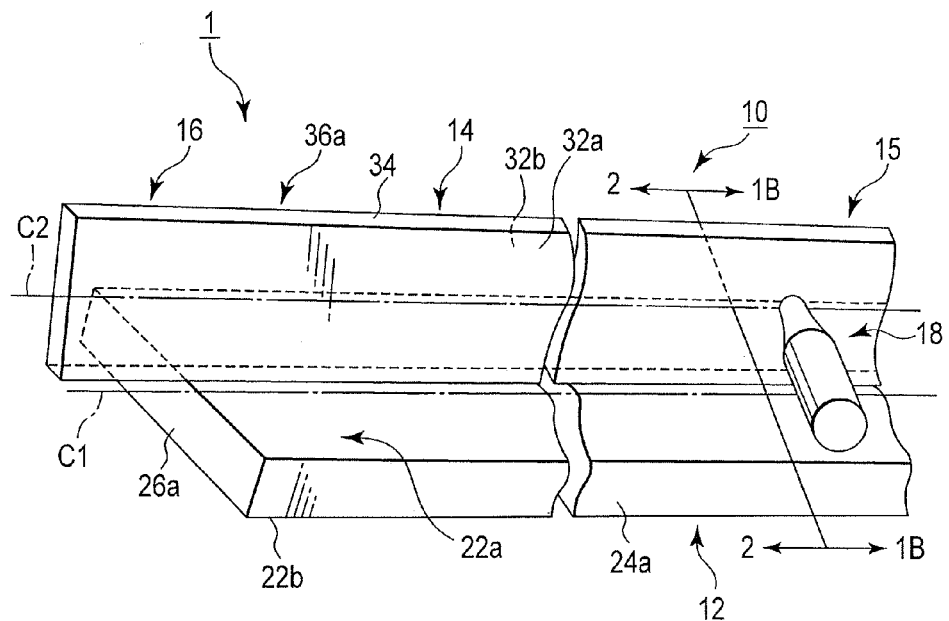
FIG. 1A is a schematic view showing an ultrasonic treatment device according to a first embodiment.

As shown in FIG. 1A, an ultrasonic surgical device or an ultrasonic treatment device 1 according to the embodiment includes a probe 10 which is configured to be an insertion section and an ultrasonic transducer (a vibration input unit) 18 which transmits ultrasonic vibration to the probe 10. The probe 10 includes an elongated base member 12 and an elongated waveguide (a vibration transmitting path) formed on the base member 12. The waveguide 14 includes a waveguide main body 15 to which ultrasonic vibration is input by the ultrasonic transducer 18 and an end effecter (a treatment portion) 16 at a distal end of the waveguide main body 15. Moreover, a tubular body (a protective member) 20 configured to protect the base member 12 and the waveguide 14 is detachably arranged outside the base member 12 and the waveguide 14. Further, the probe 10 can insert the base member 12 and the waveguide main body 15 which are covered with the tubular body 20 and the end effecter 16 protruding from the tubular body 20 into, e.g., a body cavity.

For example, a transverse cross section of the base member 12 is formed into a rectangular plate-like shape. The base member 12 includes an upper surface (a first surface) 22a and a lower surface (a second surface) 22b each having the largest area, and it also includes a left side edge portion (a third surface) 24a and a right side edge portion (a fourth surface) 24b on side surfaces of the upper surface 22a and the lower surface 22b. It is to be noted that a length of each of the upper surface 22a and the lower surface 22b of the base member 12 in the longitudinal direction is formed long, e.g., at least severalfold of that in the width direction. Further, the base member 12 has a distal end portion (one end) 26a and a proximal end portion (the other end) 26b (see FIG. 1C to FIG. 1E). The distal end portion 26a and the proximal end portion 26b of the base member 12 specify an axis (a base axis) C1 of the base member 12.

Figure 2:
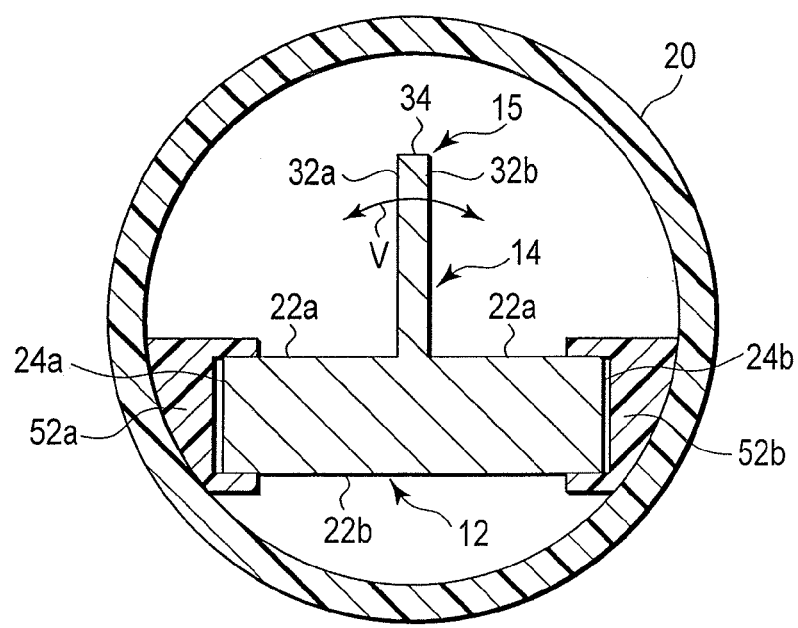
FIG. 2 is a schematic transverse cross-sectional view showing a state that the ultrasonic treatment device according to the first embodiment is cut at a position parallel to a line 2-2 in FIG. 1A.

The waveguide 14 is integrated with the upper surface 22a which is one surface (a base surface) of the base member 12, and the waveguide 14 itself is formed into, e.g., a plate-like shape having a rectangular transverse cross section. It is preferable that the waveguide main body 15 is arranged at a substantially central part of the left and right sides of the base member 12 in the width direction. Therefore, in this embodiment, as shown in FIG. 2, a transverse cross section of the probe 10 having the base member 12 and the waveguide main body 15 is formed into a substantially "T"-like shape. If such a shape is adopted, the probe 10 having the base member 12 and the waveguide 14 can be easily formed. It is to be noted that, when integrating the base member 12 and the waveguide 14, interfaces of both the members can be connected by bonding or welding such as spot welding or seam welding, or manufacture of these member can be allowed by various methods, e.g., molding such as extrusion or cutting. Therefore, the base member 12 and the waveguide 14 can be possibly made of different materials.

It is to be noted that each of the base member 12 and the waveguide 14 is formed of a metal material such as a titanium alloy.

The waveguide main body 15 has a left surface (a first surface) 32a and a right surface (a second surface) 32b each having the largest area and an upper surface (a third surface) 34 which is distal to the upper surface 22a of the base member 12. Each of the left surface 32a and the right surface 32b of the waveguide main body 15 is substantially orthogonal to the upper surface 22a of the base member 12, and the upper surface 34 of the waveguide main body 15 is substantially parallel to the upper surface 22a of the base member 12.

Figure 1B:
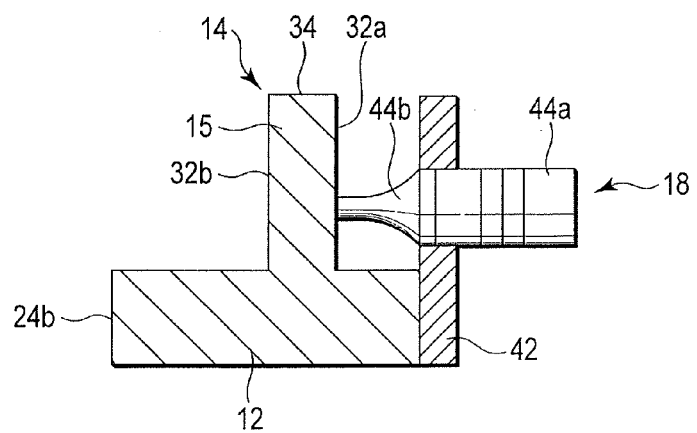
FIG. 1B is a schematic transverse cross-sectional view showing a state that an ultrasonic transducer is disposed to a waveguide of the ultrasonic treatment device according to the first embodiment as seen from a direction along a line 1B-1B depicted in FIG. 1A.
Figure 1C:
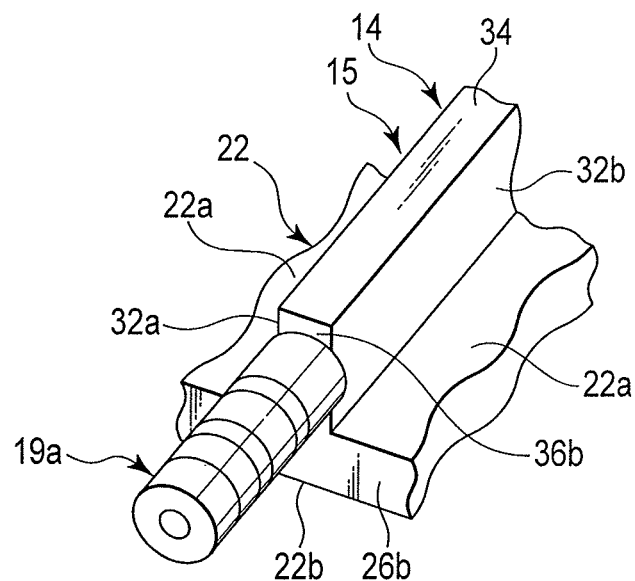
FIG. 1C is a schematic view showing a state that the ultrasonic transducer that performs torsional vibration or transverse vibration is fixed at a proximal end of the waveguide of the ultrasonic treatment device according to the first embodiment.
Figure 1D:
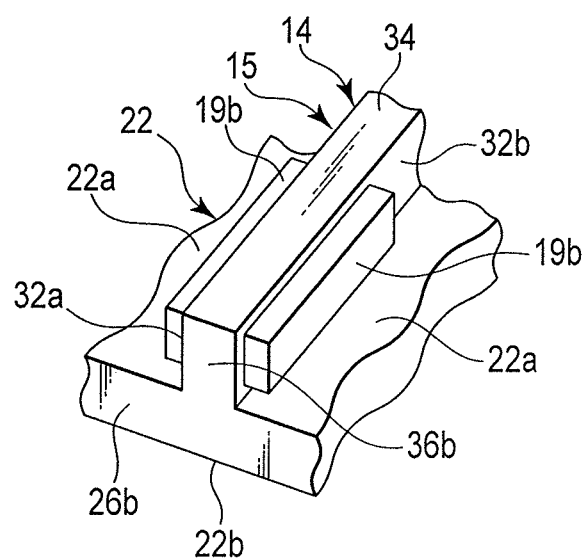
FIG. 1D is a schematic view showing a state that bimorphs are fixed on a left surface and a right surface of the waveguide of the ultrasonic treatment device according to the first embodiment.
Figure 1E:
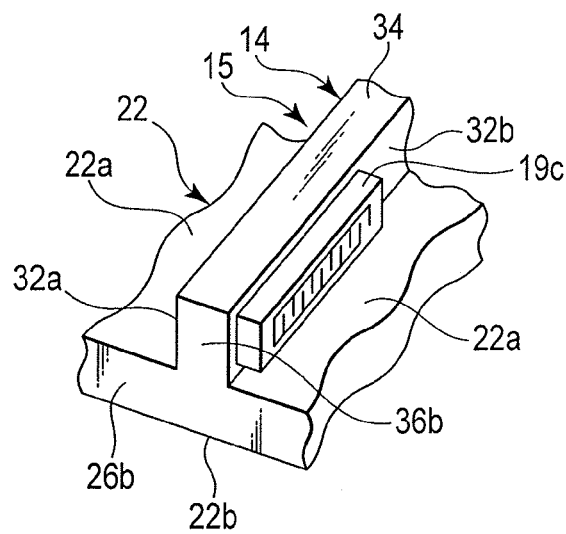
FIG. 1E is a schematic view showing a state that a surface acoustic wave vibrator is fixed on the left surface of the waveguide of the ultrasonic treatment device according to the first embodiment.

Further, the waveguide 14 has a distal end portion 36a and a proximal end portion 36b (see FIG. 1C to FIG. 1E). The distal end portion 36a and the proximal end portion 36b of the waveguide 14 define an axis C2 of the waveguide 14. Furthermore, the longitudinal axis (the base axis) C1 of the base member 12 and the longitudinal axis C2 of the waveguide 14 are parallel to each other.

The end effecter 16 according to the embodiment is provided at the distal end portion 36a of the waveguide 14 (the distal end side of the waveguide main body 15). In this embodiment, a thickness of the end effecter 16 (a width in a left-and-right direction) is equal to a distance between the left surface 32a and the right surface 32b (a thickness of the waveguide 14) of the waveguide main body 15 on the proximal side of the distal end portion 36a of the waveguide 14, and a height in an up-and-down direction of the same is equal to a distance between a lower surface (the upper surface 22a of the base member 12) and the upper surface 34 of the waveguide main body 15 (a height of the waveguide main body 15). The lower surface of the end effecter 16 in the embodiment is formed to be level with the upper surface 22a of the base member 12. The end effecter 16 protrudes frontward with respect to the distal end portion 26a of the base member 12. It is to be noted that, as will be described later, the end effecter 16 may be integrated with the upper surface 22a of the base member 12 (see FIGS. 4D, 6A, 7, 10B, and 10C). Moreover, it is also preferable that the lower surface of the end effecter 16 is level with the lower surface 22b of the base member 12.

Additionally, the waveguide 14 is an elastic body that vibrates in a direction orthogonal to the longitudinal axis C2 of the waveguide 14 when excited by the appropriate ultrasonic transducer 18, and the base member 12 is configured to have higher rigidity than the waveguide 14 so that it hardly vibrates. It is preferable that the base member 12 is formed of a vibration-retardation material, e.g., a damping material such as a damping alloy or a vibration isolating material such as a high-damping alloy.

The ultrasonic transducer 18 may be attachable to/detachable from the waveguide main body 15. In this case, it is possible to use the ultrasonic transducer 18 having various characteristics such as a size or an output depending on the intended use. However, in a relationship with the waveguide 14, it is preferable to use the ultrasonic transducer 18 that enables the thickness of the waveguide 14 to be smaller than one wavelength when the ultrasonic transducer 18 is vibrated. Further, as ultrasonic waves, standing waves, traveling waves, surface acoustic waves, and others can be used. It is to be noted that, in case of using the traveling waves, the ultrasonic vibration is attenuated by, e.g., friction of the end effecter 16 and a body tissue.

As shown in FIG. 1B, the ultrasonic transducer 18 according to this embodiment includes a Langevin type transducer 44a and a horn 44b attached to the transducer 44a. The ultrasonic transducer 18 is fixed to, e.g., the left surface 32a (which may be the right surface 32b) of the waveguide 14 by a jig 42 fixed to, e.g., the left side edge portion 24a (which may be the right side edge portion 24b) of the base member 12. In this case, the jig 42 is set to hold a position of a node of vibration when the horn 44b of the transducer 44a is vibrated. A disposing position of the ultrasonic transducer 18 with respect to the waveguide main body 15 is a position between the distal end portion 36a and the proximal end portion 36b (see FIG. 1C to FIG. 1E) of the waveguide 14. Further, the ultrasonic vibration generated by the Langevin type transducer 44a is input (transmitted) to the waveguide 14 through the horn 44b.

It is to be noted that, here, the example that the ultrasonic transducer 18 is disposed in the direction substantially orthogonal to the left surface 32a of the waveguide main body 15 has been described, but the purpose is to excite the ultrasonic vibration with a predetermined frequency and strength with respect to the waveguide 14, and hence the present invention is not restricted to this example.

Since the waveguide 14 is inserted into a body from the end effecter 16 to treat a body tissue, it is preferable to arrange the ultrasonic transducer 18 at a position closer to the proximal end side than the intermediate position between the distal end portion 36a and the proximal end portion 36b of the waveguide 14 so that the ultrasonic transducer 18 cannot be caught on a body wall or the like. The ultrasonic transducer 18 may be arranged in the tubular body 20 or arranged to pierce the tubular body 20 depending on a size of the ultrasonic transducer 18.

It is also preferable for the ultrasonic transducer 18 to excite the ultrasonic vibration with respect to the waveguide 14 by using, e.g., ultrasonic transducers 19a, 19b, and 19c depicted in FIG. 1C to FIG. 1E in addition to the ultrasonic transducer 18 depicted in FIG. 1B or in place of the ultrasonic transducer 18 shown in FIG. 1B.

FIG. 1C shows an example that the ultrasonic transducer 19a that generates torsional vibration or transverse vibration is arranged at a proximal end of the waveguide main body 15.

FIG. 1D shows an example that a pair of bimorphs 19b and 19b having a configuration that, e.g., two thin piezoelectric bodies are attached to each other are arranged on, e.g., the left surface 32a an the right surface 31b of the waveguide main body 15. In this case, the bimorphs 19b and 19b may be provided at positions facing each other to sandwich the waveguide main body 15 therebetween, may be displaced in the axial direction of the waveguide main body 15, or may be displaced in the vertical direction orthogonal to the axial direction.

FIG. 1E shows an example that the ultrasonic transducer (a surface acoustic wave element) 19c is arranged on the right surface 32b of the waveguide main body 15. Although not shown, the ultrasonic transducer (the surface acoustic wave element) 19c may be arranged on both the left surface 32a and the right surface 32b of the waveguide main body 15.

It is to be noted that, when arranging the ultrasonic transducer 19a, 19b, or 19c on the waveguide main body 15, it may be fixed by bonding with an appropriate adhesive or may be fixed by screwing.

Not only the ultrasonic transducers 18, 19a, 19b, and 19c but also various kinds of ultrasonic transducers may be arranged on the waveguide 14 to excite ultrasonic vibration. In this case, the ultrasonic transducer can be selected in accordance with a treatment.

Additionally, when the ultrasonic transducers 19a, 19b, and 19c shown in FIG. 1C to FIG. 1E are used in addition to the ultrasonic transducer 18 depicted in FIG. 1A and FIG. 1B, many vibration modes can be generated by adjusting combinations. Of course, the ultrasonic transducers 19a, 19b, and 19c alone may be combined without using the ultrasonic transducer 18.

It is to be noted that an example of using the ultrasonic transducer 18 depicted in FIG. 1A and FIG. 1B will be described hereinafter.

As shown in FIG. 2, support portions 52a and 52b that support the left side edge portion 24a and the right side edge portion 24b of the base member 12 are formed in the tubular body 20. Each of these support portions 52a and 52b is formed into, e.g., a continuous shape that continuously supports the base member 12 from the distal end portion 26a to the proximal end portion 26b of the base member 12 or a discontinuous shape that discontinuously supports the same at appropriate intervals from the distal end portion 26a to the proximal end portion 26b of the base member 12. When the support portions 52a and 52b are continuous, the support portions 52a and 52b are formed into rail-like shapes that face each other in the tubular body 20. When the support portions 52a and 52b are discontinuous, their support portions 52a and 52b face each other in the tubular body 20 or formed at staggered positions. Although not shown, a stopper that holds the distal end portion 26a of the base member 12 so that the distal end portion does not further move toward the distal side is formed at, e.g., a tip end portion of each of the support portions 52a and 52b. Furthermore, it is preferable for the base member 12 to have a configuration that it is fixed to the tubular body 20 in a state that the base member 12 is supported by the support portion 52a and 52b in the tubular body 20.

It is to be noted that the tubular body 20 and the support portions 52a and 52b may be made of a plastic material or a metal material, but using an insulating material is preferable when considering electrical insulation properties between the tubular body 20 and the base member 12 and the waveguide 14. It is also preferable for the support portions 52a and 52b to be formed of a rubber material having insulation properties.

In the thus formed probe 10, when the ultrasonic transducer 18 fixed to the waveguide 14 is vibrated, as shown in FIG. 2, the base member 12 hardly vibrates, and the waveguide 14 vibrates in the left-and-right direction along an arrow V in FIG. 2. At this moment, the base member 12 forms a vibration-retardation portion (which not only means a state no vibration is effected at all but also a state that a body tissue is not affected when brought into contact with the body tissue), and the waveguide 14 forms a vibrating portion. It is to be noted that, when the thickness of the waveguide 14 is smaller than one wavelength, a plate wave which is called a Lamb wave is produced. The plate wave transversely vibrates the waveguide 14, and the end effecter 16 at the distal end portion 36a of the waveguide 14 vibrates.

Further, when the vibrating end effecter 16 is brought into contact with a body tissue, heat is generated in the body tissue by vibration of the end effecter 16. Therefore, this ultrasonic treatment device 1 can be used to give a treatment of emulsifying, fracturing, solidifying, or incising to the body tissue.

Meanwhile, for example, in an ultrasonic treatment device disclosed in U.S. Pat. No. 6,129,735-A or U.S. Pat. No. 7,229,455-B1, a probe is generally supported by a sheath the covers the outer periphery of the probe at a position of a node of vibration of the probe. In this case, since the probe itself acts as a vibration transmitting path vibrates, to suppress an influence of the ultrasonic vibration from the probe to the sheath, there are inconveniences such as complication and increase in outside diameter due to a vibration isolating structure, energy loss due to conversion of a part of ultrasonic vibration energy into heat by an isolated part, an increase in temperature of the outside of the sheath, and others.

On the other hand, in the probe 10 according to this embodiment, the waveguide 14 alone excites by the ultrasonic vibration, and the base member 12 does not substantially vibrate. Therefore, although the base member 12 is supported by the support portions 52a and 52b of the tubular body 20, the base member 12 does not substantially vibrate, and hence the base member 12 does not exercise an influence of the ultrasonic vibration on the tubular body 20. Therefore, the ultrasonic treatment device 1 can be configured without using a special vibration isolating structure.

It is to be noted that, since the base member 12 does not substantially vibrate, even if a body tissue comes into contact with the base member 12 itself, the influence of the ultrasonic vibration can be prevented from being exerted on the body tissue that is in contact. Therefore, even if the body tissue comes into contact with the lower surface 22b of the base member 12, the influence of the ultrasonic vibration can be prevented from being exerted on the body tissue.

Furthermore, as an insertion portion (the probe 10) inserted into a body cavity or the like, a structure including the base member 12 and the waveguide 14 having the end effecter 16 can be integrally fabricated. Thus, the ultrasonic treatment device 1 according to this embodiment can have a configuration simpler than that of the ultrasonic treatment device disclosed in, e.g., U.S. Pat. No. 6,129,735-A or U.S. Pat. No. 7,229,455-B2. Therefore, in the treatment device 1 according to this embodiment, a reduction in outside diameter of the insertion portion (the probe) for the inside of a body cavity and in cost can be achieved as compared with the ultrasonic treatment device disclosed in, e.g., U.S. Pat. No. 6,129,735-A or U.S. Pat. No. 7,229,455-B2.

As described above, the elongated protruding waveguide 14 that is present on the upper surface 22a of the base member 12 (or the lower surface 22b of the base member 12) is mainly referred to as a topographic waveguide. Although the topographic waveguide is classified into a ridge type or a wedge type depending on a shape of a protruding portion (the waveguide 14 in this embodiment) on the upper surface 22a of the base member 12, the ridge type waveguide is used in this embodiment. Moreover, the ridge waveguide 14 has not only a rectangular transverse cross section but also a trapezoidal or triangular transverse cross section. That is, although the description has been given as to the waveguide having the simplest transverse cross section, i.e., the rectangular transverse cross section in this embodiment, a trapezoidal transverse cross section is also preferred. When the transverse cross section has a trapezoidal shape, there is not only a case that a width of a base side (the upper surface 22a side) (a lower bottom) of the waveguide 14 is larger than a width of an upper bottom but also a case that the width of the lower bottom is smaller than the width of the upper bottom.

Figure 3:
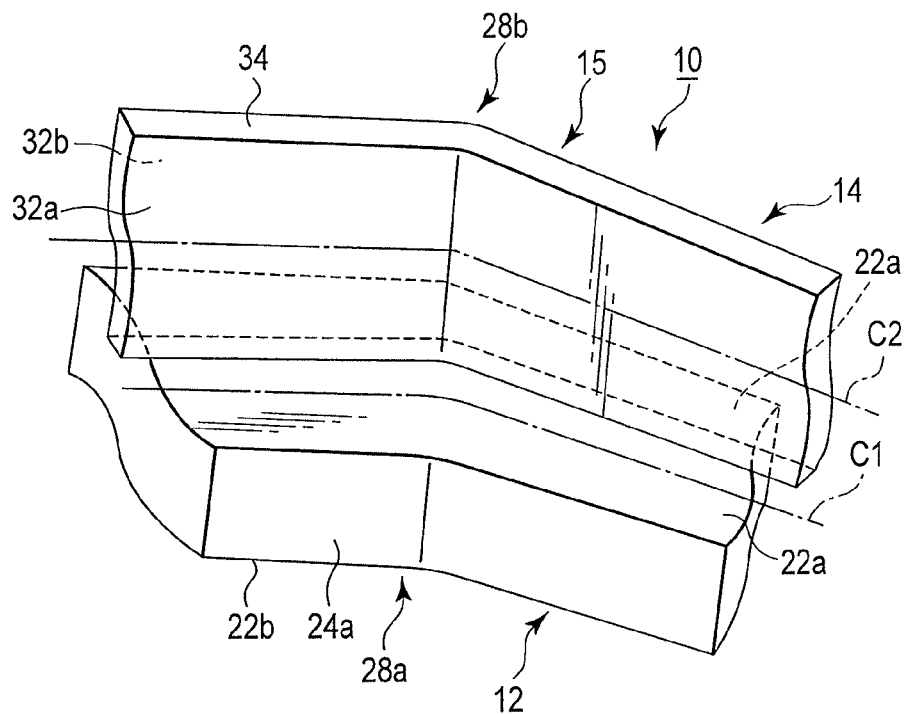
FIG. 3 is a schematic perspective view showing a state that a part of a base member and the waveguide of the ultrasonic treatment device according to the first embodiment is curved.

Additionally, the base member 12 and the waveguide 14 are not restricted to a straight shape, and they may be formed into, e.g., an S-like shape or a shape partially having a curved portion 28a or 28b (see FIG. 3). In this case, the axis C1 of the base member 12 and the axis C2 of the waveguide 14 are defined along such bent shapes. Since such a shape is allowed for each of the base member 12 and the waveguide 14, for example, even if a path from a body surface to a body tissue as a treatment target is bent, a treatment can be easily given to the body tissue as a treatment target by the treatment device 1 using the probe 10 according to this embodiment. Thus, when performing a treatment using an endoscope or a trocar, the treatment can be readily given.

On the other hand, for example, in the ultrasonic treatment device disclosed in U.S. Pat. No. 6,129,735-A or U.S. Pat. No. 7,229,455-B2, it is difficult to fabricate an external package or mechanism components of such a configuration having an S-like shape or a curved portion, and isolating vibration is also difficult. However, since the configuration of the probe 10 according to this embodiment is simple and vibration does not have to be isolated even though the probe 10 requires the tubular body 20, a weight of the treatment device 1 can be reduced, or a diameter of the probe 10 can be decreased, and hence an operative procedure can be further facilitated, thus contributing to getting rid of tiredness of an operator.

Furthermore, the first surface (the upper surface) 22a of the base member 12 itself is not restricted to a flat surface, and it may be a curved surface as long as a state the first surface 22a does not substantially vibrate when the waveguide 14 is vibrated can be maintained. In this case, if the waveguide 14 can be assuredly mounted and fixed (integrated), the first surface 22a of the base member may be formed as a curved surface which is a part of the base member 12 having, e.g., a elliptic or cylindrical transverse cross section. Moreover, forming the transverse cross section of the base member 12 into a V-like block shape or an M-like block shape is also preferable.

Additionally, although the base member 12 according to this embodiment has the rectangular transverse cross section in the above description, the left side edge portion 24a and the right side edge portion 24b do not have to be necessary flat surfaces, and they may have a shape that can be supported by the support portions 52a and 52b of the tubular body 20, e.g., a partially cylindrical shape.

Further, the distal portion (the upper surface) 34 of the waveguide 14 for the Upper surface 22a of the base member 12 has a planar shape when the ridge waveguide 14 has a rectangular or trapezoidal transverse cross section, it may have a curved surface having no edge, e.g., a partially cylindrical shape.

It is to be noted that the transverse cross section of the probe 10 is formed into a substantially "T"-like shape in the description of this embodiment, but the present invention is not restricted thereto and, for example, a substantially crisscross shape may be adopted. When the probe 10 has the substantially crisscross transverse cross section, as will be explained later in a fourth embodiment (see FIG. 7), a first waveguide 14a is formed on an upper surface 22a of a base member 12, and a second waveguide 14b is formed on a lower surface 22b of the same. In this case, a tubular body 20 is arranged on the outer side of a probe 10, and the base member 12 is supported by support portions 52a and 52b of the tubular body 20, which is preferable.

A second embodiment will now be described with reference to FIG. 4A to FIG. 5B. The second embodiment is a modification of the first embodiment, and like reference numerals denote the same members or members having the same functions as those in the first embodiment as long as possible, thereby omitting a description of these members. This can be also applied to the third embodiment to the fifth embodiment.

Figure 4A:
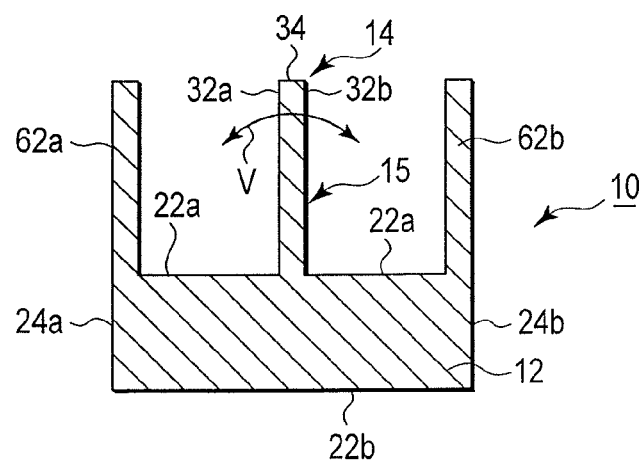
FIG. 4A is a schematic transverse cross-sectional view showing an ultrasonic treatment device according to a second embodiment.

As shown in FIG. 4A and FIG. 4B, in a probe 10 according to this embodiment, a pair of protective members (frame members) 62a and 62b are integrally formed on a left side edge portion 24a and a right side edge portion 24b of a base member 12 in parallel with a waveguide main body 15. Each of the protective members 62a and 62b is formed into a plate-like shape like a waveguide 14. An end effecter 16 is provided on a distal end side of a waveguide main body 15, and it protrudes with respect to a distal end portion 26a of the base member 12 and distal ends of the pair of protective members 62a and 62b. An ultrasonic transducer 18 can be appropriately attached or detached through a hole or a notch (not shown) formed in one or both of the pair of protective members 62a and 62b as shown in FIG. 1B.

Further, in the probe 10, the base member 12 and the waveguide main body 15 covered with the protective members 62a and 62b and the end effecter 16 protruding from the protective members 62a and 62b can be inserted into, e.g., a body cavity.

In FIG. 4A, a protruding length (a height) of the waveguide main body 15 with respect to an upper surface 22a formed as a planar surface on the base member 12 is equal to a protruding length of the protective members 62a and 62b with respect to the upper surface 22a of the base member 12. The protruding length (the height) of the waveguide main body 15 with respect to the upper surface 22a of the base member 12 may be also preferably smaller that the protruding length of the pair of protective members 62a and 62b with respect to the upper surface 22a of the base member 12. When the waveguide main body 15 and the pair of protective members 62a and 62b are formed with such a relationship, the tubular body 20 which has been described in the first embodiment and is shown in FIG. 2 does not have to be arranged on the outermost periphery of the probe 10. That is because a body tissue hardly comes into contact with an upper surface 34 of the waveguide main body 15.

Furthermore, since the protective members 62a and 62b are formed in this manner, when leading ultrasonic vibration to the end effecter 16 from the ultrasonic transducer 18 through the waveguide main body 15, an influence given from the periphery and an influence given on the periphery can be suppressed low in an intermediate path between the ultrasonic transducer 18 and the end effecter 16. Thus, for example, when treating (curing) a body tissue, sufficient vibration of an output can be provided.

On the other hand, when the protruding length (the height) of the waveguide main body 15 with respect to the upper surface 22a of the base member 12 is larger than the protruding length of the protective members 62a and 62b, to prevent the upper surface 34 of the waveguide main body 15 from coming into contact with the body tissue, providing a member that protects the waveguide main body 15, e.g., the tubular body 20 described in the first embodiment and others is preferable.

It is to be noted that, in this embodiment, as shown in FIG. 4A, the protective members 62a and 62b are formed in parallel with the waveguide main body 15 as shown in FIG. 4A in the above description, but they may not be formed in parallel when a distance between the waveguide main body 15 and each of the protective members 62a and 62b on a base side (a distance on the upper surface 22a of the base member 12) is larger than a distance between the waveguide main body 15 and each of the protective members 62a and 62b on the upper side, for example. In this case, the distance between the waveguide main body 15 and each of the protective members 62a and 62b on the upper side is excellent if the waveguide main body 15 does not come into contact with the protective members 62a and 62b when the waveguide main body 15 and the protective members 62a and 62b are deformed during use. Moreover, an outer surface of each of the protective members 62a and 62b is not restricted to a planar surface, and it may be a curved surface.

Figure 4D:
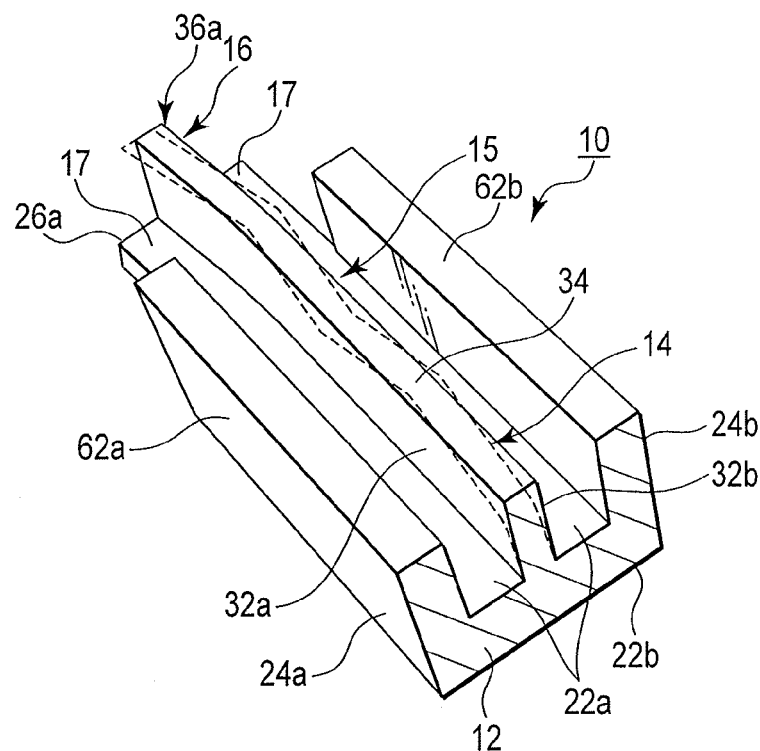
FIG. 4D is a schematic view showing the ultrasonic treatment device according to the modification of the second embodiment from an obliquely upper side and also showing a transverse cross section of the treatment device on the distal end side.

Additionally, in the first embodiment and the second embodiment, the end effecter 16 shown in FIG. 1A protrudes on the left side (the distal end side of the treatment device 1) in FIG. 1A with respect to the distal end portion 26a of the base member 12. On the other hand, as shown in FIG. 4D, it is preferable that a tip end of the end effecter 16 of the waveguide 14 and a distal end portion 26a of the base member 12 are provided on the same surface. That is, it is also preferable that the distal end portion 26a of the base member 12 is extended to the tip end of the end effecter 16 (the tip end of the waveguide 14) to form an extended portion 17 on the base member 12, and a distal end portion 36a of the waveguide path 14 is used as the end effecter 16. Further, it is also preferable that the distal end of the end effecter 16 and the distal end portion 26a of the base member 12 protrude with respect to the distal ends of the pair of protective members 62a and 62b described in the second embodiment. In other words, the distal ends of the pair of protective members 62a and 62b are placed at positions on a proximal end side with respect to the tip end of the end effecter 16 (the distal end portion 36a of the waveguide 14) and the distal end portion 26a of the base member 12.

Even if the distal end of the probe 10 is formed in this manner, the end effecter 16 at the distal end portion 36a of the waveguide 14 can be likewise used as described in the first embodiment and the second embodiment.

Figure 5A:
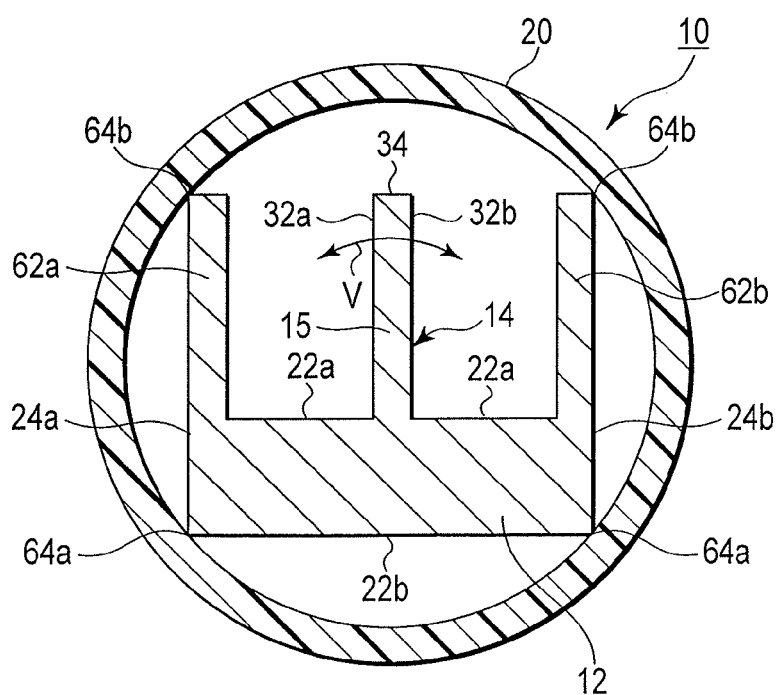
FIG. 5A is a schematic transverse cross-sectional view showing an ultrasonic treatment device according to further modification of the second embodiment.

When the protruding length of each of the protective members 62a and 62b with respect to the upper surface 22a of the base member 12 is formed to be sufficiently long in accordance with the protruding length (the height) of the waveguide 14 with respect to the upper surface 22a formed as the planar surface of the base member 12, it is possible to simplify the configuration of the member that protects the waveguide 14, e.g., the tubular body 20 described in the first embodiment. That is, the tubular body 20 shown in FIG. 5A is able to be solely used as a protection member of the probe 10. In this case, it is preferable that corner portions 64a which are formed of the lower surface 22b of the base member 12 and the pair of protective members 62a and 62b and which are long in the axial direction of the probe 10, and corner portions 64b which are formed at positions parallel to the left side edge portion 24a and the right side edge portion 24b of the pair of protective members 62a and 62b, which are provided at positions apart from the lower surface 22b and which are long in the axial direction of the probe 10 are in contact with the inner peripheral surface of the tubular body 20 having a cylindrical shape. In this case, the probe 10 may be movable in the axial direction with respect to the tubular member 20 or movable in the circumferential direction, or the probe 10 may be fixed to the tubular body 20. It is to be noted that no gap is formed between the corner portions 64a and 64b and the inner peripheral surface of the tubular body 20 in FIG. 5A, but forming a gap between one or more corner portions 64a and 64b and the inner peripheral surface of the tubular body 20 is also preferable. A support portion (e.g., an antivibration member such as a rubber material) that prevents relative movement of the probe 10 and the tubular body 20 may be arranged in the gap between the corner portions 64a and 64b and the inner peripheral surface of the tubular body 20.

Furthermore, the probe 10 may have a configuration shown in FIG. 5B. The probe 10 shown in FIG. 5B includes a base member 12a having an upper surface (a first surface) 22a, a waveguide 14 formed on the upper surface 22a, and a protective member 62 formed on left and right edge portions 24a and 24b of the base member 12.

A transverse cross section of the base member 12 shown in FIG. 5B is formed into a substantially semicircular shape. Further, the protective member 62 is formed into a substantially halfpipe-like shape integrally with the base member 12. In this case, an outer peripheral surface 22c of the base member 12a and the protective member 62 fulfill the same role as the tubular body 20 described in the first embodiment.

In addition, although not shown, an ultrasonic transducer may be arranged in the protective member 62 or arranged to pierce the protective member 62.

In this example, since the base member 12a does not substantially vibrate even though the waveguide 14 vibrates, it is possible to suppress an influence of the vibration of the waveguide 14 on a body tissue which is in contact with the base member 12a or the protective member 62 due to the ultrasonic vibration.

Figure 6B:
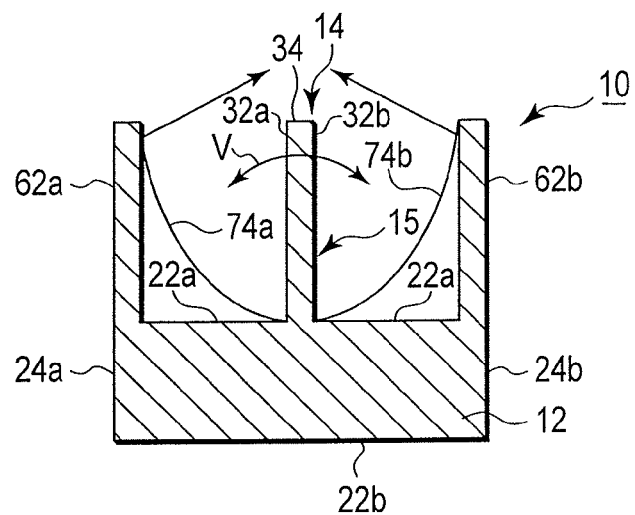
FIG. 6B is a schematic transverse cross-sectional view showing an ultrasonic treatment device according to a modification of the third embodiment.

A third embodiment will now be described with reference to FIG. 6A and FIG. 6B.

As shown in FIG. 6A, here, as different from the second embodiment shown in FIG. 4B, an outer periphery of an end effecter 16 is covered with a pair of frame bodies (protective members) 72a and 72b. These frame bodies 72a and 72b are integrally formed at a distal end portion 26a of a base member 12 and tip ends of a pair of protective members 62a and 62b.

Furthermore, reflecting surfaces (ultrasonic focusing mirrors) 74a and 74b, each of which is formed of a smooth concaved surface, are formed between the frame bodies 72a and 72b and the end effecter 16, respectively.

These reflecting surfaces 74a and 74b reflect ultrasonic vibration emitted from the end effecter 16 when the periphery of the end effecter 16 is arranged in a liquid, e.g., water including blood produced from a body tissue, for example. At this time, although depending on forming angles of the reflecting surfaces 74a and 74b, the reflecting surfaces 74a and 74b focus ultrasonic energy on the front side of the end effecter 16 in FIG. 6A and/or the upper side of the end effecter 16 in FIG. 6B rather than in the end effecter 16 itself. That is, the reflecting surfaces 74a and 74b are formed to focus the ultrasonic waves on a body tissue as a treatment target rather than the end effecter 16.

Since the energy in an ultrasonic treatment generated from the end effecter 16 can be reflected on the reflecting surfaces 74a and 74b and used as described above, the energy can be applied to the inside tissue rather than a contact surface of the body tissue.

It is to be noted that the pair of protective members 62a and 62b and the frame bodies 72a and 72b are used in this description, but the reflecting surfaces 74a and 74b can be likewise formed in case of using the protective member 62 shown in FIG. 5B.

A fourth embodiment will now be described with reference to FIG. 7 to FIG. 10C.

Figure 7:
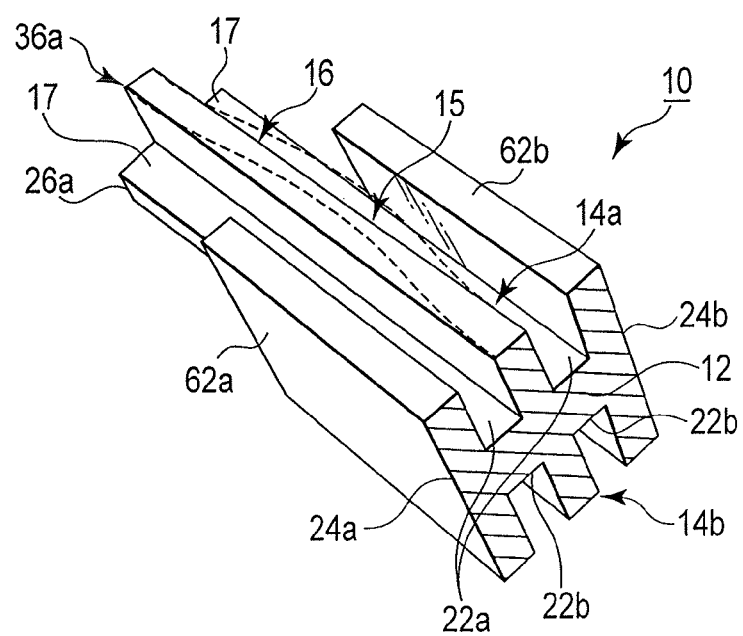
FIG. 7 is a schematic view showing an ultrasonic treatment device according to a fourth embodiment from an obliquely upper side and also showing a transverse cross section of the treatment device on a distal end side.

As shown in FIG. 7, a probe 10 according to this embodiment includes a base member 12, a pair of waveguides 14a and 14b, and a pair of protective members 62a and 62b. The base member 12 includes an upper surface 22a and a lower surface 22b, one waveguide (a first waveguide) 14a is formed on the upper surface 22a, and the other waveguide (a second waveguide) 14b is formed on the lower surface 22b. An end effecter 16 is formed at respective distal end portions 36a of the waveguides 14a and 14b. Further, an extended portion 17 is formed at a tip end portion of the base member 12. Furthermore, the pair of protective members 62a and 62b are formed on a left side edge portion 24a and a right side edge portion 24b of the base member 12. The protective members 62a and 62b are formed to be same level with or higher than the waveguides 14a and 14b from the upper surface 22a and the lower surface 22b of the base member.

It is to be noted that, in this embodiment, the probe 10 is symmetrically formed with respect to a non-illustrated surface (a neutral surface) of the upper surface 22a and the lower surface 22b of the base member 12.

Figure 8A:
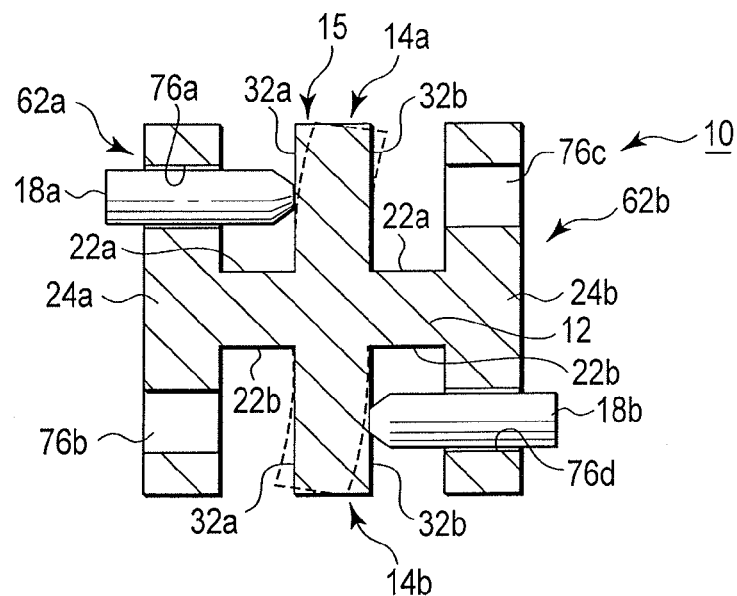
FIG. 8A is a schematic transverse cross-sectional view showing the ultrasonic treatment device according to the fourth embodiment in a state that a pair of waveguides vibrate in opposite phases with respect to a base member.
Figure 8B:
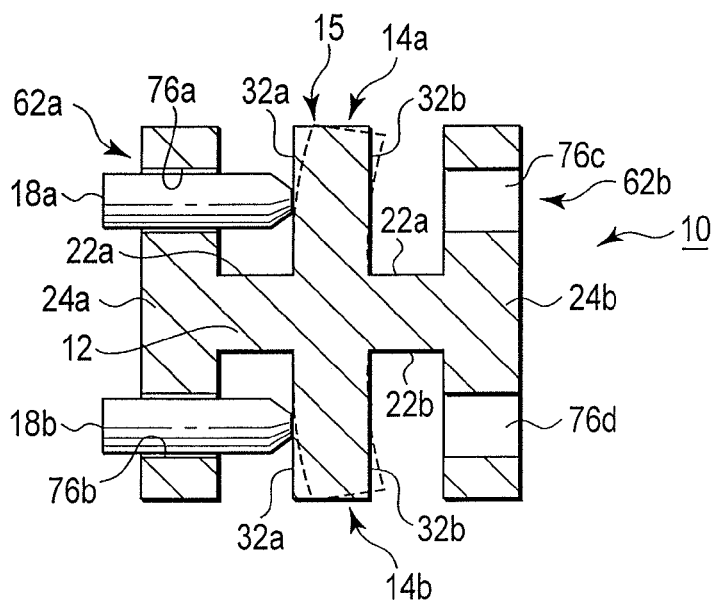
FIG. 8B is a schematic transverse cross-sectional view showing the ultrasonic treatment device according to the fourth embodiment in a state that the pair of waveguides vibrate in the same phase with respect to the base member.

Moreover, the waveguides 14a and 14b may be vibrated in opposite phases shown in FIG. 8A, or they may be vibrated in the same phase shown in FIG. 8B.

In case of vibrating the waveguides 14a and 14b in the opposite phases, for example, one torsion type ultrasonic transducer is used, or two longitudinal vibration type ultrasonic transducers 18a and 18b shown in FIG. 8A are used. In case of vibrating the waveguides 14a and 14b in the opposite phases, for example, the torsion type ultrasonic transducer is arranged at a position of one waveguide (e.g., the upper waveguide 14a) of the two waveguides 14a and 14b close to the base member 12 (a base-side position). Alternatively, as shown in FIG. 8A, one longitudinal vibration type ultrasonic transducer 18a is arranged on a left surface 32a of the waveguide 14a provided on the upper side of the base member 12 and the other longitudinal vibration type ultrasonic transducer 18b is arranged on a right surface 32b of the waveguide 14b provided on the lower side of the base member 12 through two openings 76a and 76d of four openings 76a, 76b, 76c, and 76d in the protective members 62a and 62b. It is to be noted that these ultrasonic transducers 18a and 18b are preferably the same in performance.

When outputs are generated from these ultrasonic transducers 18a and 18b at the same time, the two waveguides 14a and 14b vibrate in the opposite phases. Therefore, the end effecter 16 vibrate in directions that are opposite on the upper side and the lower side of the base member 12. That is, the entire end effecter 16 can be vibrated in a torsional direction.

In case of vibrating the waveguides 14a and 14b in the same phase, for example, the two longitudinal vibration type ultrasonic transducers 18a and 18b shown in FIG. 8B are used. The one ultrasonic transducer 18a is arranged on, e.g., the left surface 32a of the upper waveguide 14a through the opening 76a of the protective member 62a, and the other ultrasonic transducer 18b is arranged on, e.g., the left surface 32a of the lower waveguide 14b through the opening 76b of the protective member 62a.

When outputs are generated from these ultrasonic transducers 18a and 18b at the same time, the two waveguides 14a and 14b vibrate in the same phase. Therefore, the end effecter 16 vibrates in a direction orthogonal to the upper surface 22*a* and the lower surface 22*b* of the base member 12. Further, the waveguides 14*a* and 14*b* are vibrated in the same phase.

It is to be noted that, when output timing of each of the two ultrasonic transducers 18*a* and 18*b* is shifted or magnitudes of outputs are set, the vibration in the same phase or the opposite phases can be appropriately produced with respect to the waveguides 14*a* and 14*b*.

Further, although an appropriate thickness is required for each of the protective members 62*a* and 62*b*, when male screw portions (not shown) are formed on the outer peripheral surfaces of the ultrasonic transducers 18*a* and 18*b* and female screw portions (not shown) are formed in the openings 76*a*, 76*b*, 76*c*, and 76*d*, the ultrasonic transducers 18*a* and 18*b* can be easily fixed to a treatment device 10.

As shown in FIG. 9A and FIG. 9B, it is preferable to form, e.g., a semicircular opening 78 at a position between the end effecter 16 and the distal end portion 26*a* of the base member 12. If this opening is formed, since the vibration is not restricted at the distal end portion 26*a* of the base member 12, the vibration from the ultrasonic transducer can be effectively transmitted to the end effecter 16. That is, presence of the opening 78 formed on the boundary between a proximal end of the end effecter 16 and the distal end portion 26*a* of the base member 12 enables reducing loss of the vibration. It is to be noted that the shape of the opening 78 is not restricted to the semicircular shape, and a substantially triangular shape can be adopted. In this case, like FIG. 9B, the distal end portion 26 of the base member 12 is determined as a bottom surface, and a height direction of the triangle is arranged on the distal end side of the end effecter 16.

Figure 10A:
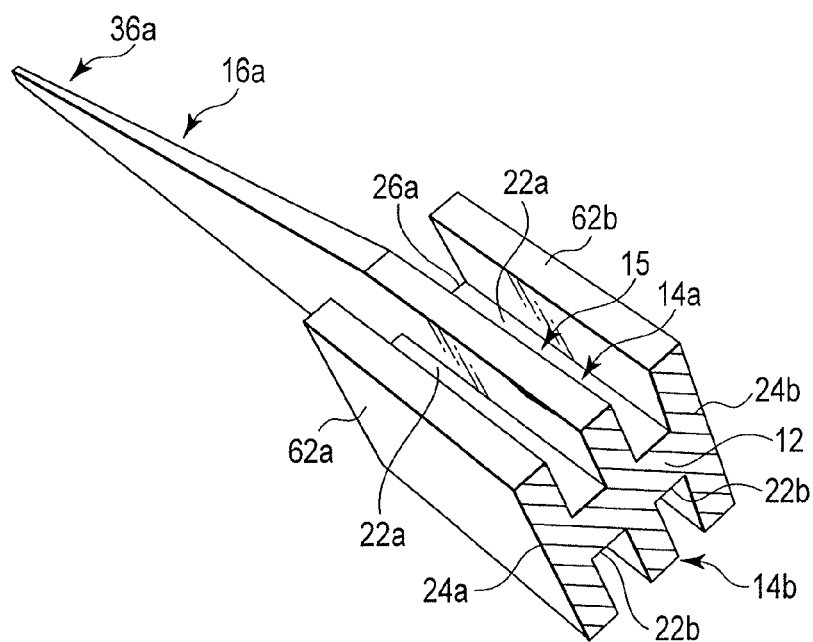
FIG. 10A is a schematic view showing an ultrasonic treatment device according to further modification of the fourth embodiment from an obliquely upper side and also showing a transverse cross section of the treatment device on the distal end side.

Further, as shown in FIG. 10A, using the tapered end effecter 16*a* is also preferable. It is preferable to form the end effecter 16*a* into not only a tapered shape that the end effecter 16 is linearly tapered from a tip end of a waveguide main body 15 toward the tip end of the end effecter 16 as shown in FIG. 10A but also a tapered shape that steps are formed at appropriate intervals so that the end effecter 16*a* can be gradually tapered. When the probe 10 having such an end effecter 16*a* is used, a therapy device (the treatment device 1) aimed at a fine portion can further exercise effects.

Figure 10B:
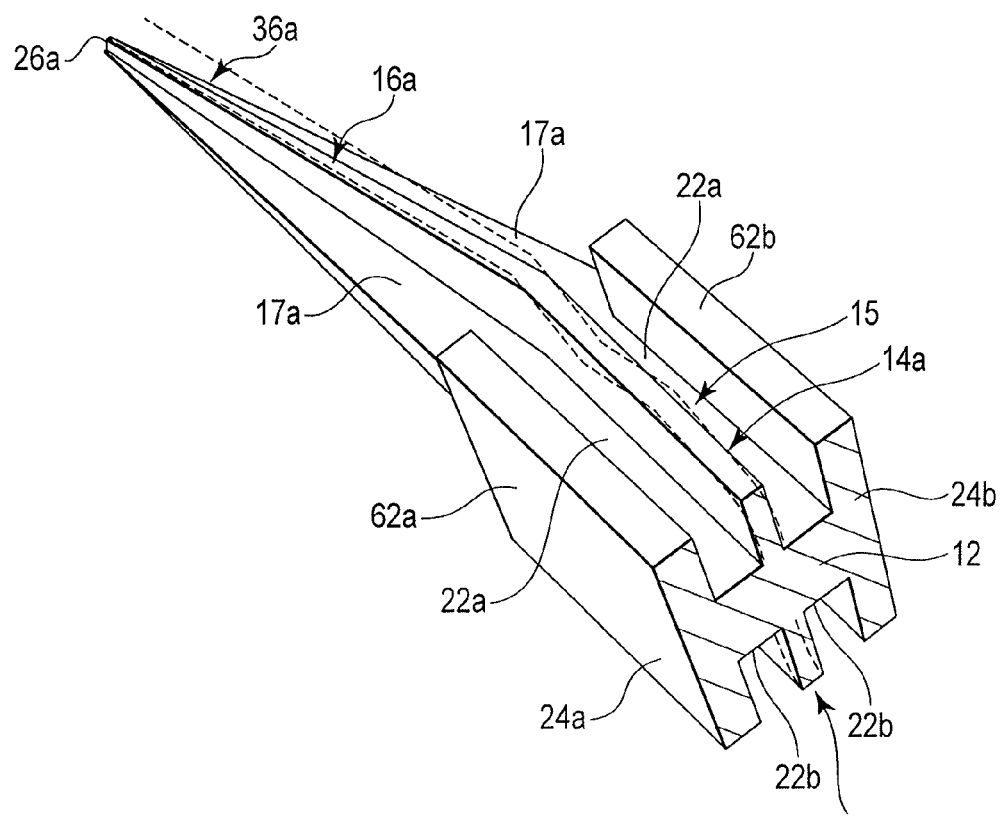
FIG. 10B is a schematic view showing an ultrasonic treatment device according to further modification of the fourth embodiment from an obliquely upper side and also showing a transverse cross section of the treatment device on the distal end side.

Like FIG. 4D and FIG. 7, FIG. 10B shows an example that an extended portion 17*a* that the distal end portion 26*a* of the base member 12 is protruded with respect to tip ends of the protective members 62*a* and 62*b* is formed. In this case, the extended portion 17*a* is tapered as getting away from the protective members 62*a* and 62*b*. That is, it is preferable to taper the base member 12 from the protective members 62*a* and 62*b* toward the distal end portion 26*a* of the base member 12. Further, a width of the distal end portion 26*a* of the base member 12 is preferably equal to or slightly larger than a thickness of the end effecter 16.

Figure 10C:
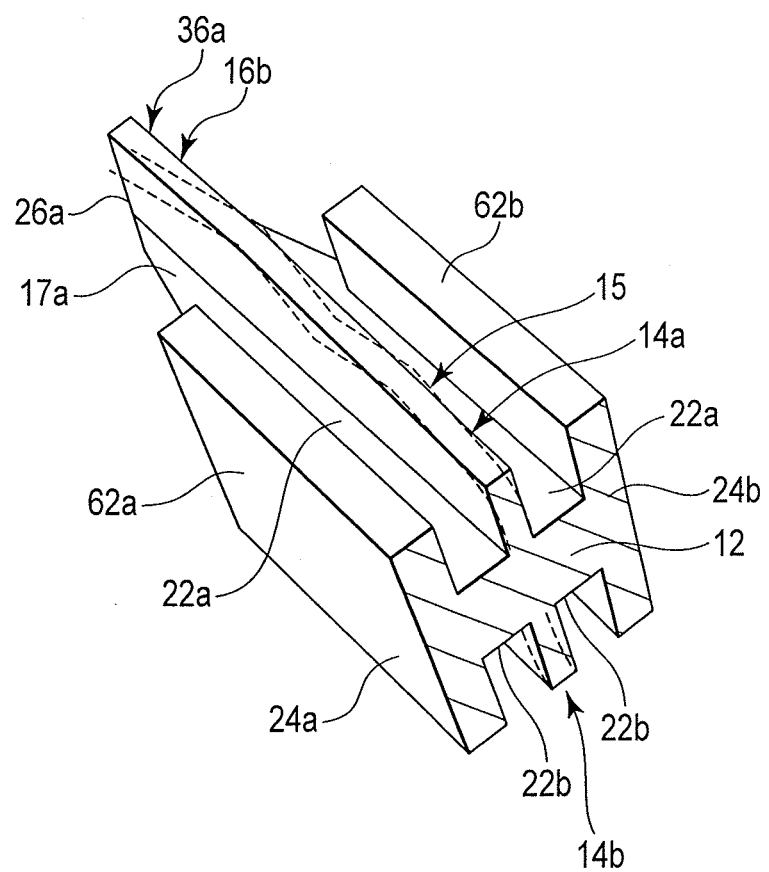
FIG. 10C is a schematic view showing an ultrasonic treatment device according to further modification of the fourth embodiment from an obliquely upper side and also showing a transverse cross section of the treatment device on the distal end side.

An end effecter 16*b* shown in FIG. 10C is an example obtained by cutting the tip end of the end effecter 16*a* depicted in FIG. 10B and forming the distal end portion 26*a* of the base member 12 to have the same thickness as the end effecter 16*b*. In this case, a height direction of the tip end of the end effecter 16*b* is higher than the height direction of the tip end of the end effecter 16*a* shown in FIG. 10B.

It is to be noted that the waveguide 14 shown in each of FIG. 10B and FIG. 10C is preferably symmetrically formed with respect to the base member 12.

Furthermore, although the treatment device 10 is symmetrical with respect to the non-illustrated surface (the neutral surface) between the upper surface 22*a* and the lower surface 22*b* of the base member 22 in this embodiment in the above description, the treatment device 10 does not have to be symmetrical with respect to the non-illustrated surface (the neutral surface) between the upper surface 22*a* and the lower surface 22*b* of the substrate 22 when the waveguides 14*a* and 14*b* have different heights or the waveguides 14*a* and 14*b* have different thicknesses, for example.

Furthermore, although the pair of plate-like protective members 62*a* and 62*b* facing each other are used in this embodiment in the above description, it is possible to adopt not only a state that the protective members 62*a* and 62*b* are connected to each other above the base member 12 (see FIG. 5B) but also a non-illustrated state that the protective members 62*a* an 62*b* are connected to each other below the base member 12.

A fifth embodiment will now be described with reference to FIG. 11A and FIG. 11B.

As shown in FIG. 11A, an ultrasonic treatment device 1 according to this embodiment includes a probe 10 having a later-described configuration, a jaw (a body tissue grasping portion) 92 that can be come into contact with or separated from an end effecter 16*a* of the probe 10, and a wire 94 that moves the jaw 92. The probe 10 includes a base member 12, a pair of waveguides 14*a* and 14*b* having the tapered end effecter 16*a* (see FIG. 10A) at distal ends thereof, and a pair of protective members 62*a* and 62*b*.

In addition, it is preferable to arrange, e.g., a halfpipe-like guide member 96 shown in FIG. 11B on a lower surface or the like of the protective member 62*a* and hold the wire 94.

In this embodiment, the jaw 92 is supported on the outer side of the pair of protective members 62*a* and 62*b* so that the jaw 92 can turn through a pin 98. Moreover, the jaw 92 is connected to a tip end of the wire 94, and the wire 94 is extended toward a proximal end side of the base member 12. Thus, when the wire 94 is moved (pulled) toward the proximal end side, a distal end of the jaw 92 moves closer to the end effecter 16*a*. When the wire 94 is moved toward a distal end side of the base member 12, the distal end of the jaw 92 moves away from the end effecter 16*a*. Therefore, the jaw 92 can grasp/release a body tissue between itself and the end effecter 16*a*.

In this embodiment, the jaw 92 can be arranged on the protective members 62*a* and 62*b* that do not substantially vibrate like the base member 12. Therefore, the tubular body 20 described in the first embodiment is not required, and a member that supports the jaw on a distal end thereof when the tubular body 20 is arranged is not required either. Therefore, the number of components can be reduced as compared with the ultrasonic treatment device in U.S. Pat. No. 6,129,735-A or U.S. Pat. No. 7,229,455-B2, and hence an advantage of easily achieving miniaturization can be obtained.

A modification of the fifth embodiment will now be described with reference to FIG. 12.

Figure 12:
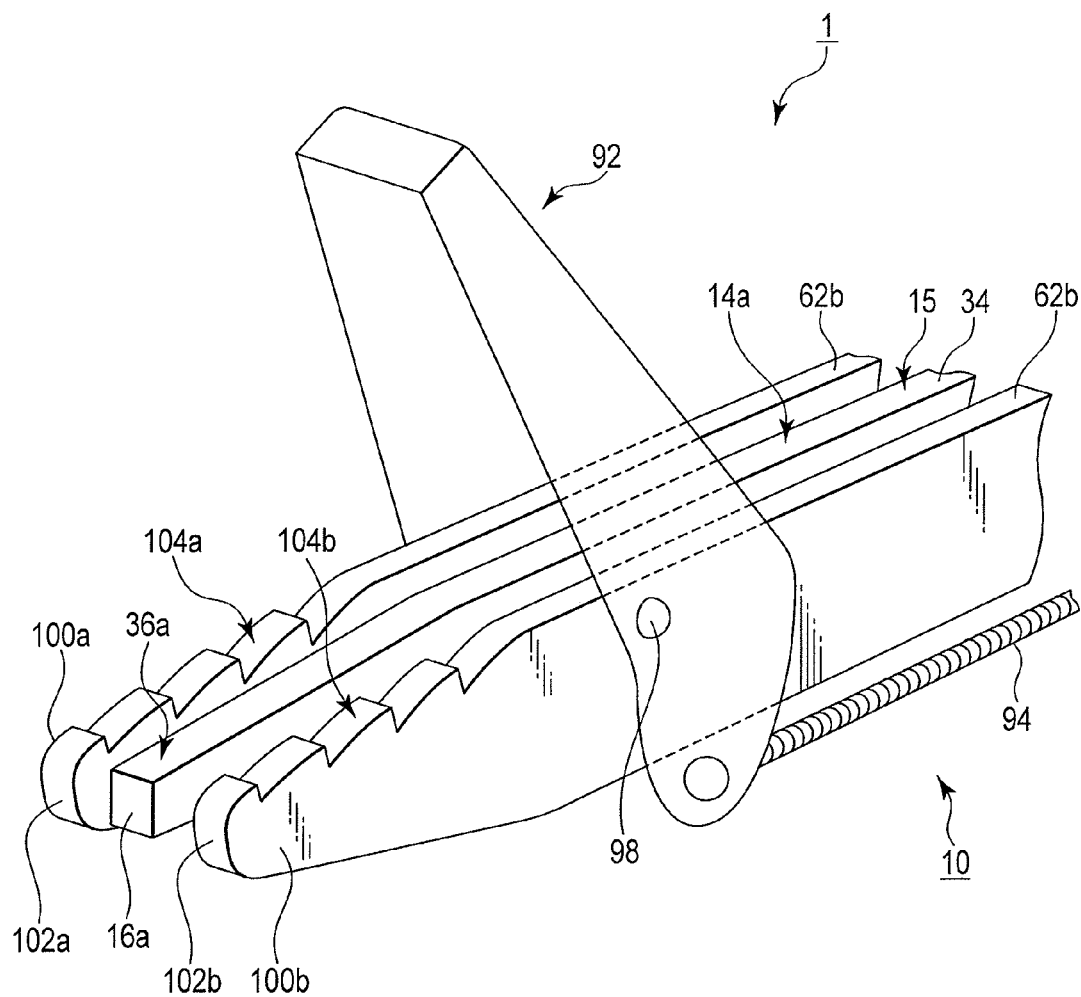
FIG. 12 is a schematic perspective view showing a distal end side of an ultrasonic treatment device according to a modification of the fifth embodiment.

An ultrasonic treatment device 1 shown in FIG. 12 includes protruding portions 100*a* and 100*b* obtained by protruding protective members 62*a* and 62*b* to positions close to a tip end of an end effecter 16*a*. It is preferable to form curved surfaces 102*a* and 102*b* on tip ends of the protruding portions 100*a* and 100*b* so that these tip ends cannot be caught on a body tissue. Slip stoppers 104*a* and 104*b* are formed on surfaces of the protruding portions 100*a* and 100*b* that are close to the jaw 92, respectively. It is to be noted that tooth rows are formed as the slip stoppers 104*a* and 104*b* in FIG. 12. Besides the tooth rows, the slip stoppers 104*a* and 104*b* may be, e.g., satin finished surfaces as long as they have an antislip function. Since such slip stoppers 104*a* and 104*b* are formed at the positions close to the end effecter 16*a*, when a body tissue is sandwiched between the jaw 92 and the slip stoppers 104*a* and 104*b*, i.e., when the body tissue is sandwiched between the jaw 92 and the end effecter 16a, the body tissue can be assuredly fixed to the end effecter 16a.

In this modification, when the slip stoppers 104a and 104b configured to grasp the body tissue are integrally formed on the protruding portions 100a and 100b of the protective members 62a and 62b, the body tissue can be assuredly grasped without increasing the number of components. Therefore, a treatment can be assuredly given to the body tissue by using the end effecter 16a.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A probe which is configured for a treatment device which is configured to treat a body tissue using ultrasonic vibration, the probe comprising:
   a base member which includes a top surface and a bottom surface on a reverse side of the top surface each defined by a first longitudinal direction and a width direction orthogonal to the first longitudinal direction and a width of the width direction being shorter than a length of the first longitudinal direction, the base member being configured not to have the ultrasound vibration coupled thereto;
   a plate-shaped waveguide main body which is provided on the top surface protrudes with respect to the top surface, and has a width smaller than the width of the top surface in the width direction and a height with respect to the top surface larger than the width of the waveguide main body, and is extended along a second longitudinal direction which is away from the first longitudinal direction of the top surface, the ultrasonic vibration being input to the waveguide main body; and
   an end effector which is provided at a tip end portion of the waveguide main body and which is configured to treat the body tissue by the ultrasonic vibration transmitted through the waveguide main body,
   wherein the base member is a member which is more resistant to transmitting the ultrasonic vibration than the waveguide main body, and
      the waveguide main body is over most of its length dimension located on the top surface of the base member,
   wherein, a transverse cross section orthogonal to the longitudinal direction of the base member in a state that the base member is combined with the waveguide main body, has a T-shape.

2. The probe according to claim 1, wherein each of the waveguide main body and the end effector has a distal end portion, a proximal end portion, and a longitudinal axis defined by the distal end portion and the proximal end portion, and is configured to vibrate in a direction orthogonal to the longitudinal axis of the waveguide main body by the ultrasonic vibration.

3. The probe according to claim 1, wherein, a transverse cross section orthogonal to the longitudinal direction of the base member in a state that the base member is combined with the waveguide main body, has a crisscross shape.

4. The probe according to claim 1, comprising a protective member which is configured to protect the waveguide main body at an edge portion of the top surface and the bottom surface of the base member in the width direction.

5. The probe according to claim 4, wherein the end effector is configured to protrude with respect to tip ends of the base member and the protective member.

6. The probe according to claim 4, wherein at least one of the top surface and the bottom surface of the base member and the protective member has a reflecting surface which is configured to reflect and focus the ultrasonic vibration transmitted from the waveguide main body.

7. The probe according to claim 4, wherein a grasping portion configured to grasp the body tissue between itself and the end effector is arranged on the protective member.

8. The probe according to claim 4, wherein the protective member has a tubular shape.

9. The probe according to claim 4, wherein the protective member is integrated with the base member.

10. The probe according to claim 1, further comprising at least one ultrasonic transducer which is detachable in a direction deviating from a direction along which the waveguide main body is extended.

11. A probe which is configured for a treatment device which is configured to treat a body tissue using ultrasonic vibration, the probe comprising:
    a base member which includes a top surface and a bottom surface on a reverse side of the top surface, each defined by a first longitudinal and a bottom surface on a reverse side of the top surface each defined by a first longitudinal direction and a width direction orthogonal to the first longitudinal direction and a width of the width direction being shorter than a length of the first longitudinal direction, the base member being configured not to have the ultrasound vibration coupled thereto;
    a waveguide main body which is arranged on the top surface of the base member protrudes with respect to the top surface and has an elongated plate shape wherein a width of the waveguide main body is smaller than a height of the waveguide main body, smaller than a width of the top surface of the base member and smaller than one wavelength of the ultrasonic vibration and is extended along a second longitudinal direction which is away from the first longitudinal direction of the to surface, the ultrasonic vibration being input to the waveguide main body; and
    an end effector which is configured to protrude with respect to a tip end of the base member, which is provided on a distal end portion of the waveguide main body, and which is configured to apply a plate wave generated by the ultrasonic vibration to the body tissue,
    wherein;
    the base member is a member which is more difficult to transmit the ultrasonic vibration than the waveguide main body, and
    the waveguide main body is configured to transmit the plate wave to the end effector when the ultrasonic vibration is input from at least one surface of the waveguide main body,
    wherein, a transverse cross section orthogonal to the longitudinal direction of the base member in a state that the base member is combined with the waveguide main body, has a T-shape.

12. The probe according to claim 11, wherein the waveguide main body includes: a distal end portion; a proximal end portion; and a longitudinal axis defined by the distal end portion and the proximal end portion, and the probe further comprises an ultrasonic transducer which is detachable in a direction deviating from the longitudinal direction of the waveguide main body.

13. The probe according to claim 11, wherein a protective member which is configured to protect the waveguide main body is arranged on the base member.

14. An actuation method of an ultrasonic probe comprising:
- an ultrasonic transducer which is configured to generate an ultrasonic vibration, a base member which includes a top surface and a bottom surface on a reverse side of the to surface each defined by a first longitudinal direction and a width direction orthogonal to the first longitudinal direction and a width of the width direction being shorter than a length of the first longitudinal direction, the base member being configured not to have the ultrasound vibration coupled thereto;
- a plate-shaped waveguide main body which is provided on the top surface protrudes with respect to the to surface, and has a width smaller than the width of the to surface in the width direction and a height with respect to the top surface larger than the width of the waveguide main body, and is extended along a second longitudinal direction which is away from the first longitudinal direction of the top surface, the ultrasonic vibration being input to the waveguide main body; and
- an end effector which is provided at a tip end portion of the waveguide main body and which is configured to treat the body tissue by the ultrasonic vibration transmitted through the waveguide main body,
- wherein the base member is a member which is more resistant to transmitting the ultrasonic vibration than the waveguide main body, and
- the waveguide main body is over most of its length dimension located on the top surface of the base member, and
- wherein, a transverse cross section orthogonal to the longitudinal direction of the base member in a state that the base member is combined with the waveguide main body, has a T-shape, the actuation method of the ultrasonic probe comprising:
- a step of generating plate wave by applying ultrasonic vibration with the ultrasonic transducer to a proximal end portion the waveguide main body in a state that a width of the waveguide main body is smaller than one wavelength of the ultrasonic vibration, and preventing influence of the ultrasonic vibration on the base member while the ultrasonic vibration is applied to the waveguide main body; and
- a step of vibrating the end effector by the plate wave.

* * * * *